United States Patent [19]
Hoffmann

[11] 3,959,272
[45] May 25, 1976

[54] AMINOALKYL ESTERS OF 2-ANILINO-NICOTINIC ACIDS

[75] Inventor: Charles Hoffmann, Enghien-les-Bains, France

[73] Assignee: Societe Anonyme dite: Hexachime, France

[22] Filed: June 4, 1973

[21] Appl. No.: 366,610

[30] Foreign Application Priority Data
June 7, 1972  France .............................. 72.20490

[52] U.S. Cl. .................... 260/247.2 B; 260/268 H; 260/293.69; 260/295.5 R; 424/248; 424/250; 424/266
[51] Int. Cl.² ........................................ C07D 295/00
[58] Field of Search ......... 260/295.5, 293.69, 268 H

[56] References Cited
FOREIGN PATENTS OR APPLICATIONS
1,802,777  6/1969  Germany ..................... 260/247.2 B

*Primary Examiner*—Paul J. Killos

[57] ABSTRACT

Amino alkyl 2-anilino nicotinates of the formula:

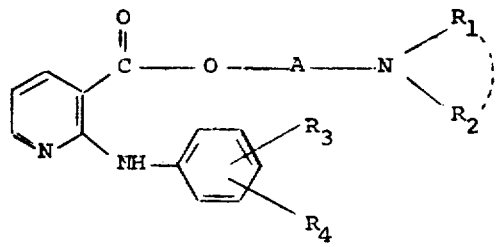

in which A is $CH_2CH_2$ or $CH_2C(CH_3)_2$, $R_1$ and $R_2$ are both methyl or together with the adjacent nitrogen make up a piperidino, morpholino or N-methylpiperazino ring, and $R_3$ and $R_4$ are both hydrogen or are both methyl in positions 2 and 3 or 2 and 6 of the phenyl nucleus or $R_3$ is chlorine in position 2, 3 or 5 and $R_4$ is methyl in position 2, 4 or 6 of the phenyl nucleus and their acid addition salts, made by reaction of the corresponding amino alkyl chloride with an alkali metal salt of the appropriate 2-anilino nicotinic acid, have interesting analgesic, anti-inflammatory, and psychotropic properties.

1 Claim, No Drawings

AMINOALKYL ESTERS OF 2-ANILINO-NICOTINIC ACIDS

This invention relates to amino alkyl esters of 2-anilino nicotinic acids and their preparation.

In U.S. Pat. No. 3,708,481 there are described amino alkyl esters of 2-anilino nicotinic acids of the formula:

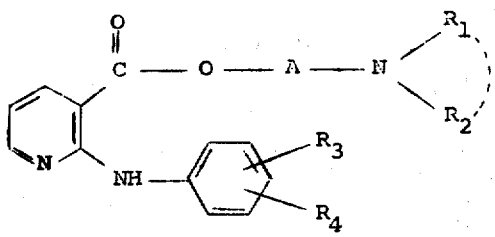

and their non-toxic acid addition salts in which A represents a straight chain or branched lower alkylene radical, $R_1$ and $R_2$ taken seperately represent lower alkyl radicals, or, taken together with the nitrogen atom to which they are attached, represent a five or six membered nitrogen-containing saturated heterocyclic structure which can contain another hetero-atom, and $R_3$ and $R_4$ are identical or different and each represents a hydrogen or halogen or a lower alkyl, lower alkoxy or lower halogeno alkyl radical. These compounds may be prepared by one of two methods.

In the first method an equimolecular mixture of the appropriate 2-anilino nicotinic acid and amino alkyl chloride are heated together in an appropriate solvent, for example, in isopropanol under reflux for 3–8 hours. This process gives the hydrochloride of the desired base.

In the second method an acid chloride of the appropriate 2-anilino nicotinic acid is reacted with an amino alkanol, again with the production of the hydrochloride of the desired ester.

According to the present invention, the amino alkyl esters of 2-anilino nicotinic acids of formula I in which A is $CH_2CH_2$ or $CH_2C(CH_3)_2$, $R_1$ and $R_2$ are both methyl or together with the adjacent nitrogen make up a piperidino, morpholino or N-methylpiperazino ring, and $R_3$ and $R_4$ are both hydrogen or both methyl in positions 2 and 3 or 2 and 6 of the phenyl nucleus, or $R_3$ is chlorine in position 2, 3 or 5 and $R_4$ is methyl in position 2, 4 or 6 of the phenyl nucleus, and their non-toxic acid addition salts, are made by reacting an alkali metal salt of a 2-anilino nicotinic acid of the formula:

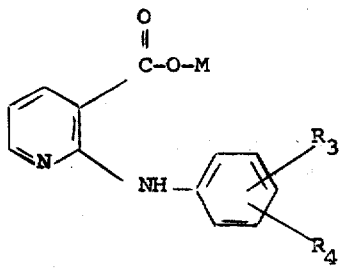

in which M is an alkali metal with an amino alkyl chloride of the formula:

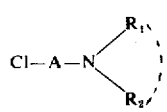

and optionally converting the base obtained into a non-toxic acid addition salt thereof. Preferably, the sodium or potassium salt of the 2-anilino nicotinic acid is used and the reaction is carried out at elevated temperature in a non-plar solvent, e.g. toluene, in order to reduce the risk of transesterification. When the reaction is complete the reaction mixture is cooled, the precipitated alkali metal chloride filtered off, and the desired product isolated by evaporation of the resulting solution under reduced pressure. Conversion of the base obtained into an acid addition salt thereof may be carried out in known manner.

The esters produced by this process and their non-toxic acid addition salts are new. Especially valuable are those esters in which A is $CH_2CH_2$ and

is morpholino, and their non-toxic acid addition salts.

The following Examples illustrates the invention. Nixylic acid is 2-(2,3-dimethylanilino)-nicotinic acid.

EXAMPLE 1

β-Morpholino ethyl nixylate

A solution of sodium ethoxide is prepared by dissolving sodium (28 g) in absolute ethanol (850 ml). Nixylic acid (295 g) is then added and slowly dissolves. The alcohol is then evaporated to dryness and the resulting sodium nixylate suspended in anhydrous toluene. β-Morpholino ethyl chloride (191 g) is added with stirring and the mixture is heated under reflux for 3½ hours. After cooling, the sodium chloride formed is removed by filtration and the toluene then evaporated under reduced pressure. The oil obtained crystallises on cooling to give 366 g of a yellow product, mp 61° to 62°C. After recrystallisation from petroleum ether, the desired product is obtained as brilliant yellow spangles, mp 66° to 68°C.

Analysis: calculated for $C_{20}H_{25}N_3O_3$, N % = 11.82; found N % = 12.0

This base forms a monohydrochloride sparingly soluble in water and a very soluble dihydrochloride. The dihydrochloride decomposes at 230°C.

Analysis: calculated for $C_{20}H_{25}N_3O_3$. 2H Cl, N % = 9.80, Cl % = 16.55; found N % = 9.78, Cl % = 16.52

The citrate and the succinate may be prepared by dissolving equimolecular quantities of the above described ester and anhydrous citric or succinic acid in the minimal quantity of methanol and then evaporating the latter under reduced pressure at a temperature below 45°C. Potentiometric titration with perchloric acid shows that both salts have a purity of 99%. The succinate melts at 128°C.

EXAMPLE 2

β-Piperidino ethyl nixylate

Proceeding as in Example 1 but using β-piperidino ethyl chloride in place of β-morpholino ethyl chloride, the base obtained melts at 60.5°C (capillary) after recrystallisation from petroleum ether.

Analysis : calculated for $C_{21}H_{27}N_3O_2$, N % = 11.88; found N % = 12.07

EXAMPLE 3

2-Dimethylamino-2-methylpropyl nixylate

Proceeding as in Example 1 but using 2-dimethylamino-2-methylpropyl chloride in place of β-morpholino ethyl chloride, the ester is obtained as an oil, which may be converted into the monohydrochloride by reaction with a solution of hydrogen chloride in diethyl ether. This monohydrochloride melts at about 185°C and is soluble in water.

Analysis: calculated for $C_{20}H_{27}N_3O_2$. H Cl, N % = 11.11, Cl % = 9.38; found N % = 11.28, Cl % = 9.27

EXAMPLE 4

β-(N-methylpiperazino)ethyl nixylate

Proceeding as in Example 1 but using 1-(β-chloroethyl)-4-methylpiperazine in place of β-morpholino ethyl chloride, an oil is obtained which is converted into the dihydrochloride by addition of normal aqueous hydrochloric acid. The water is removed in vacuo and the residue dissolved in absolute ethanol and again evaporated to dryness. The pale yellow solid product obtained is recrystallised from methanol and then melts at 231-232°C (capillary).

Analysis: calculated for $C_{21}H_{28}N_4O_2$ 2 H Cl, N % = 12.72, Cl % = 16.08; found N % = 12.88, Cl % = 16.17

EXAMPLE 5

β-Morpholino ethyl 2-anilino nicotinate

This compound is prepared as described in Example 1 using 2-anilino nicotinic acid in place of nixylic acid. The base is converted into its monohydrochloride which melts at 165°–168°C.

Analysis: Cl % calculated 9.74; found 9.70 & 9.74

EXAMPLE 6

β-Morpholino ethyl 2-(2,6-dimethylanilino) nicotinate

Proceeding as in Example 1 but using 2-(2,6-dimethylanilino)nicotinic acid in place of nixylic acid, the base obtained melts at 98°C. Potentiometric titration with perchloric acid shows that it is essentially 100% pure.

EXAMPLE 7

β-Morpholino ethyl 2-(3-chloro-4-methylanilino) nicotinate

Proceeding as in Example 1 but using 2-(3-chloro-4-methylanilino)nicotinic acid in place of nixylic acid, the base obtained melts at 70°C.

EXAMPLE 8

β-Morpholino ethyl 2-(2-methyl-5-chloroanilino) nicotinate

Proceeding as in Example 1 but using 2-(2-methyl-5-chloroanilino)nicotinic acid in place of nixylic acid, the base obtained melts at 86°C. Potentiometric titration with perchloric acid shows that it is essentially 100% pure.

EXAMPLE 9

β-Morpholino ethyl 2-(2-chloro-6-methylanilino) nicotinate

Proceeding as in Example 1 but using 2-(2-chloro-6-methylanilino)nicotinic acid in place of nixylic acid, the base obtained melts at 126°C. The monohydrochloride, which is soluble in water, decomposes at about 205°C.

Analysis: calculated for $C_{19}H_{22}N_3O_3Cl$. H Cl, Cl % ionisable = 8.59, total = 17.19; found Cl % ionisable = 8.6, total = 17.0

The amino alkyl esters of the present invention are useful as analgesics, and have anti-inflammatory and psychotropic properties. Their properties have been demonstrated by the following tests.

Anti-inflammatory activity

The method used was as follows.

The anti-inflammatory activity was measured on oedema provoked by carragenin in the rat. Groups of six male rats each weighing 120 to 130 g received the compound under test orally in suspension in "tween 80", half the dose being given 2 hours before and the other half ½ hour before the subcutaneous plantar injection of 0.05 ml of a 1 % carragenin solution. The volume of the injected paw was measured by plethysmography at regular intervals. Table 1 below gives the percentage inhibition of the oedema with reference to untreated controls.

TABLE 1

| mg/kg Orally | percentage in inhibition of oedema caused by product of | | | | | | | | |
|---|---|---|---|---|---|---|---|---|---|
| | Ex.1 | Ex.2 | Ex.3 | Ex.4 | Ex.5 | Ex.6 | Ex.7 | Ex.8 | Ex.9 |
| 16 | 16 | — | — | — | — | — | — | — | 7 |
| 32 | 20 | — | — | — | — | — | — | — | — |
| 64 | 34 | 6 | — | 0 | — | 0 | — | 0 | 20 |
| 128 | 45 | 42 | 0 | 50 | 0 | 13 | 2 | — | — |
| 256 | 61 | 70 | 72 | 62 | 17 | 36 | 29 | 36 | 39 |
| 512 | — | — | 67 | — | 71 | 80 | 53 | — | — |

Analgesic acticity

This activity was measured by Siegmund's test in mice and Randall and Selitto's test in the rat.

Siegmund's Test

Groups of six mice received the compound under test orally 1 hour before intraperitoneal injection of 0.2 ml of an 0.02% of solution of phenylbenzoquinone. The number of painful reactiors from the fifth to the tenth minute after the injection of phenylbenzoquinone was counted. Table II below shows the percentage inhibition of these reactions with reference to untreated controls.

TABLE II

| mg/kg Orally | percentage in inhibition of reactions caused by product of ||||||||| 
|---|---|---|---|---|---|---|---|---|---|
| | Ex.1 | Ex.2 | Ex.3 | Ex.4 | Ex.5 | Ex.6 | Ex.7 | Ex.8 | Ex.9 |
| 4 | 10 | — | — | — | — | — | — | — | — |
| 8 | 26 | — | — | — | — | — | — | — | — |
| 16 | 26 | — | — | — | — | — | — | — | 14 |
| 32 | 45 | 24 | — | 8 | 16 | — | 14 | — | 8 |
| 64 | 64 | 48 | 31 | 33 | 38 | 23 | 33 | — | 8 |
| 128 | 83 | 69 | 49 | 69 | 57 | 39 | 55 | — | 37 |
| 256 | 95 | — | 75 | 84 | 83 | 69 | 55 | 18 | 66 |
| 512 | — | — | — | — | — | 100 | 77 | 74 | — |

Randall and Selitto's Test

Groups of ten male rats each weight 120 to 140 g received by subcutaneous plantar injection 0.05 ml of a 5% aqueous suspension of beer yeast. 2 Hours after this treatment they received the compound under test orally and 1 hour after administration of this compound the paw which had been injected and the contralateral paw were subjected to increasing pressure. The appearance of the pain threshold was noted. This method was used with the compounds which had been shown more active in the Siegmund Test. The following Table III shows the percentage increase in the pain threshold as a function of the dose administered.

TABLE III

| mg/kg Orally | percentage increase of pain threshold caused by compound of ||||||||
|---|---|---|---|---|---|---|---|---|
| | Ex.1 with/without yeast || Ex.2 with/without yeast || Ex.3 with/without yeast || Ex.4 with/without yeast ||
| 8 | 15 | 37 | — | — | — | — | — | — |
| 16 | 68 | 29 | — | — | 33 | — | 0 | 8 |
| 32 | 90 | 51 | — | — | 42 | 0 | 31 | 30 |
| 64 | 83 | 72 | 5 | 0 | 66 | 2 | 27 | 46 |
| 128 | 120 | 101 | 30 | 52 | 41 | 11 | 61 | 38 |
| 256 | 161 | 126 | 87 | 33 | — | 0 | 16 | 10 |

Laparotomy

Rats weighing 110 to 130 g each received the product of Example 1 (as the hydrochloride) by intraperitoneal injection. 10 or 30 Minutes after the treatment, the animals are examined to see:

1. If they allow themselves to remain lying on their backs;
2. if they do not struggle;
3. if they tolerate an incision into the skin; and
4. if they tolerate an incision into the muscle. If an animal submits without reaction it is counted as zero, and if it reacts it is counted as one. The total score is calculated for each dosage. The following table gives the percentage protection and the number of sleeping rats.

| mg/kg Intraperitoneally | Animals observed 30 min. after treatment ||| Animals observed 10 min. after treatment |||
|---|---|---|---|---|---|---|
| | Number of rats | Percentage protection | Number of sleeping rats | Number of rats | Percentage protection | Number of sleeping rats |
| 16 | 6 | 0 | 0 | 12 | 6 | 0 |
| 32 | 6 | 0 | 0 | 12 | 34 | 0 |
| 64 | 24 | 34 | 0 | 24 | 62 | 0 |
| 128 | 12 | 62 | 8 | 12 | 96 | 0 |
| 256 | 6 | 92 | 6 | — | — | — |
| ED₅₀ | 100 mg/kg intraperitoneal ||| 44 mg/kg intraperitoneal |||

Stimulation of dental pulp in the rabbit

24 Hours before the test, each incisor of the rabbit is drilled 1 mm below the gum to a depth of about 1 mm. The next day, the animals are placed in restraining boxes and stimulating electrodes are placed in position. The threshold of reaction to the electrical stimulation (at 30 Hz; 10 ms; for 1 s) is measured by the munching reaction of the rabbits. The product of Example 1 was administered intravenously and its effect on the pain threshold was measured at regular intervals after treatment. The following results were obtained.

| Number of Rabbits | Dose of compound tested mg/kg intravenously | Threshold in volts |||||||
|---|---|---|---|---|---|---|---|---|
| | | T-1h & T-30 min | 15 | 30 min | 1 h | 1h30 | 2 h | 2h30 |
| 15 | 2.5 | 2.26 | 3.12 | 3.02 | 3.20 | 3.61 | 3.54 | 3.33 |
| | % | | 38 | 33 | 41 | 59 | 56 | 47 |
| 15 | 5 | 2.54 | 4.97 | 4.80 | 4.02 | 4.05 | 3.31 | 2.94 |
| | % | | 95 | 88 | 58 | 59 | 30 | 15 |
| 15 | 10 | 2.65 | 4.62 | 5.80 | 4.49 | 4.05 | 3.72 | 3.29 |
| | % | | 74 | 118 | 69 | 52 | 40 | 24 |

PSYCHOTROPIC ACTIVITY

Hypnotic activity

The compounds under test were administered to rats or mice intraperitoneally. The loss of the righting reflex was noted and the duration of sleep measured objectively with reference to the loss of the righting reflex. The compounds under test were also administered by slow perfusion to dogs. The moment when the dog fell asleep and the duration of sleep was noted. Only the product of Example 1 caused sleep. The results obtained with this compound are shown in the following table.

TABLE VI

| mg/kg intraperitoneally | Percentage inhibition of tonic convulsions caused by product of | | | | | | | |
|---|---|---|---|---|---|---|---|---|
| | Ex.1 | Ex.2 | Ex.3 | Ex.4 | Ex.5 | Ex.7 | Ex.8 | Ex.9 |
| 4 | — | 0 | — | — | 0 | — | — | — |
| 8 | 0 | 16 | 0 | — | 16 | — | — | — |
| 16 | 12 | 5 | 5 | 0 | 33 | — | — | — |
| 32 | 21 | 22 | 16 | 0 | 33 | — | 0 | — |
| 64 | 62 | 72 | 83 | 58 | 16 | 0 | 17 | 0 |
| 128 | 95 | 100 | 100 | 91 | 33 | 9 | 33 | 100 |
| 256 | — | — | — | — | 100 | 59 | 67 | — |
| 512 | — | — | — | — | — | — | 100 | — | mg/kg of cardiazole. The action of the compound under test on the tonic convulsion phase was observed. Table VI below shows the percentage inhibition of the tonic convulsions as a function of the doses administered.

TABLE IV

| Number of animals mice | mg/kg intraperitoneally | % of sleeping animals |
|---|---|---|
| 24 | 50 | 0 |
| 24 | 75 | 46 |
| 30 | 100 | 57 |
| 18 | 125 | 84 |
| 24 | 200 | 92 |
| 6 | 250 | 100 |

Two dogs each weighing 11 kg. received intravenously 48 mg/kg of the product of Example 1 perfused at the rate of 1 mg/kg/minute. Sleep appeared at the end of 25 minutes and lasted for 15 minutes. The animals were sleepy for 1 hour after the end of the perfusion. They eventually recovered and were completely normal the next day.

Escape test

Groups of 8 mice were placed in sub groups of 4 in an enclosure from which they could escape by an inclined plane. The number of attempts to escape during 5 minutes were counted half an hour after intraperitoneal administration of the compound under test. The following V shows the percentage inhibition, with reference to untreated controls, in the number of attempts to escape as a function of the dose administered.

Potentiation of stereotypes by amphetamine

The compound under test was administered to groups of 5 rats intraperitoneally. Thirty minutes afterwards, 5 mg/kg of dexamphetamine sulphate was injected intraperitoneally. The duration of the phenomenon is counted at regular intervals from 0 to 4 and the counts are added up. The results given in the following Table VII only relate to those compounds which potentiate the stereotypes caused by amphetamine.

TABLE VII

| mg/kg intraperitoneally | Sum of the counts using product of | | | |
|---|---|---|---|---|
| | Ex.1 | Ex.5 | Ex.8 | Ex.10 |
| 8 | 14 | — | — | 45 |
| 16 | 18 | 14 | — | 70 |
| 32 | 21 | — | 89 | 76 |
| 64 | 33 | 22 | 87 | 92 |
| 128 | 43 | — | 161 | 121 |
| 256 | — | 44 | 195 | — |

The results of the pharmocological tests described above show that the compounds of the invention have analgesic and anit-inflammatory properites and are psychotropic agents in the general sense and, more particularly, hypnotics, tranquillisers, anti-convulsants and anti-depressants. The new compounds show these properties in the tests usually used to determine them. The product of Example 1 is the most active compound according to the results obtained.

ACTIVITY ON CARDIOVASCULAR PARAMETERS IN THE DOG

Unsorted dogs of either sex weighing 8 to 17 kg and anaesthetised by chloralose in solution in polyethylene glycol 300 (0.12 g/kg) were respirated artificially using

TABLE V

| mg/kg intraperitoneally | Percentage inhibition caused by product of | | | | | | | | |
|---|---|---|---|---|---|---|---|---|---|
| | Ex.1 | Ex.2 | Ex.3 | Ex.4 | Ex.5 | Ex.6 | Ex.7 | Ex.8 | Ex.9 |
| 8 | +6 | +6 | −16 | +2 | — | — | — | — | — |
| 16 | +3 | −21 | −15 | −11 | −12 | −13 | −48 | — | −19 |
| 32 | −8 | −43 | −30 | −37 | −5 | −20 | — | −25 | −22 |
| 64 | −51 | −80 | −67 | −61 | −23 | −35 | −62 | −52 | −59 |
| 128 | −100 | −100 | −95 | −95 | −20 | −74 | — | −62 | −100 |
| 256 | — | — | — | — | −78 | −100 | −96 | −83 | — |

Antagonism of convulsions produced by cardiazole

Groups of 6 mice received the compound under test 30 minutes before introperitoneal injection of 160 a Bird pump (Mark 7). The carotid arterial blood pressure was measured with the aid of a Statham P 23 dB device. The left ventricular pressure is measured with the same device connected by a supple catheter introduced by the femoral artery and pushed into the left ventricle. The cardiac rhythm is measured from the signals of the carotid pressure. The myocardial contractile force is measured using a strain gauge (Apelab) attached to the right ventricle. All the parameters are recorded on a Beckman polygraph. Two series of dogs are used to test the cardiovascular activity: 5 dogs atropinised (1 mg/kg intravenously) and bivagotomised; and a second series of 4 intact dogs. The product of Example 1 was injected through the saphena vein and the duration of the injection was 2 minutes.

Atropinised and bivagotomised dogs

During the injection or one to two minutes afterwards, a slight increase in the cardiac rhythm (2–16 beats per minute according to the dose), a slight increase in the contractile force (which was measured in 2 dogs only), and a slight increase in the arterial pressure at doses of 1 and 2 mg/kg (average $\pm$ 6%) or a reduction in blood pressure at doses of 4 mg/kg and above, were observed. Two minutes after the injection, a hypotension proportional to the dose injected was observed. The following Table VIII gives the variations of the recorded parameters and their significance according to the t test (* $p<0.05$; ** $p<0.01$).

isoprenaline in 3 dogs out of 5 only if the animals have been atropinised and bivagotomised.

ACUTE TOXICITY

The mortality 7 days after administration of the product of Example 1 was observed in lots of 10 rats and 10 mice. In the rat, the LD 50 on oral administration was greater than 2350 mg/kg and by intraperitoneal injection was 875 mg/kg. In the mouse, the LD 50 on oral administration was 1600 mg/kg, on intraperitoneal administration 700 mg/kg, and on intravenous administration was 110 mg/kg.

TOXICITY AFTER INTRAVENOUS PERFUSION

The product of Example 1 was perfused in the dog at a dosage of 50 mg/minute by the saphena vein. Cardiac arrest was produced by a dose of 344 mg/kg.

CHRONIC TOXICITY

Six beagle dogs (3 male and 3 female) received each day for 3 months 150 mg/kg of the product of Example 1. No mortality was observed, and the weights of the dogs remained normal. No modification attributable to the treatment was observed in the biochemical and hematological characteristics of the animals. Histological examination of the organs shows that they were

TABLE VIII

| No. of dogs per dose | Dose mg/kg intravenously | Systolic blood pressure % | Diastolic blood pressure % | Average blood pressure % | Time necessary to reach the lowest blood pressure | Duration of reduced blood pressure | Change in cardiac rhythm beats per minute |
|---|---|---|---|---|---|---|---|
| 5 | 1 | −3,3±3 | −4±2 | −4±2 | 4 to 8 | 10 to 30 | 0 to 10 |
| 2 | 2 | −12 | −12 | −12 | 8 to 11 | 30 | 0 to 14 |
| 5 | 5 | −13±3* | −15±4* | −14±3** | 5 to 13 | 15 to 60 | −8 to −20 |
| 5 | 8 | −24±5** | −27±5** | −26±5** | 5 to 18 | (not recorded | −8 to −20 |
| 2 | 16 | −30 | −32 | −31 | 4 to 10 | (> 30 | −18 to −24 |

The variations of the left ventricular blood pressure (measured in two dogs only) followed the variations of the arterial blood pressure.

Intact dogs

No biphasic action on the recorded parameters was observed after injection of the product of Example 1 in different dosages to intact dogs. The following Table IX gives the variations of the parameters recorded and their significance according to the t test (* $p<0.05$;  $p<0.01$; * $p<0.001$).

normal.

15 Male and 15 female rats received everyday for 3 months 800 mg/kg of the product of Example 1 orally. Only 4 rats died.

The product of Example 1 has been administered to patients suffering from post-operative pain following bone surgery. 10 Patients received the compound at a daily dosage of 150 mg orally. Complete or partial analgesia was felt by 5 patients and slight analgesia by a further 4. When administered intramuscularly at a dosage of 20 to 100 mg per day to 9 patients, the prod-

TABLE IX

| No.of dogs per dose | Dose mg/kg intravenously | Systolic pressure | Diastolic pressure | Average pressure | Time necessary for the establishment of minimum blood pressure | Duration of the hypotension | Alteration in cardiac rhythm beats per minute |
|---|---|---|---|---|---|---|---|
| 4 | 1 | −8±4.6 | −10±5.7 | −9±5.2 |  | 30 | −1 |
| 4 | 4 | −15±5.3 | −18±5.5* | −16±5.4 | 5 | 60 | −15 |
| 2 | 8 | −34 | −41 | −38 | to | not recorded | −22 |
| 4 | 16 | −45±7** | −57±3.8*** | −54±4.3** | 8 | >50 | −37 |

The product of Example 1 is without action on the activity of noradrenaline. It potentiates the action of uct of Example 1 produced complete analgesia in 5, partial analgesia in 2 and slight analgesia in the remaining 2. When adminstered inravenously in a dosage of 50 to 100 mg per day by slow injection to 13 patients, the product of Example 1 produced complete analgesia in 9 patients, moderate analgesia in 3, and no analgesia in the remaining patient. Eight patients received the product of Example 1 rectally in a dosage of 300 mg per day. Six experienced strong analgesia, one moderate analgesia, and the last one no analgesia.

The invention includes within its scope pharmaceutical compositions comprising one or more of the active compounds of the invention in association with a compatible pharmaceutically acceptable carrier. Such compositions may be made up in a form suitable for oral, parenteral or rectal administration using conventional carriers and diluents. Using the product of Example 1, each unit dosage may contain, in the case of capsules, 150 mg, in the case of drinkable solutions, 30 mg/ml, in the case of ampoules 100 to 300 mg, and in the case of suppositories, 300 mg. These weights are all expressed as free base, but in the case of aqueous solutions, (drinkable solutions and ampoules) it is convenient to administer the product as the citrate.

I claim:

1. The compound β-morpholinoethyl 2(2,3-dimethylanilino)nicotinate or a non-toxic acid addition salt thereof.

* * * * *